United States Patent [19]

Berazosky et al.

[11] 4,086,273

[45] Apr. 25, 1978

[54] PROCESS FOR MAKING BETA-AMINOETHYL SULFIDES FROM ALIPHATIC MERCAPTANS AND 2-OXAZOLINES

[75] Inventors: Sandra Berazosky; Mark E. Kaiser, both of Midland, Mich.

[73] Assignee: The Dow Chemical Company, Midland, Mich.

[21] Appl. No.: 676,765

[22] Filed: Apr. 14, 1976

[51] Int. Cl.$^2$ .................... C07C 102/00; C07C 85/00
[52] U.S. Cl. .......................... 260/561 S; 260/307 F; 260/307 G; 260/558 S; 260/559 T; 260/562 S; 260/399; 260/583 EE
[58] Field of Search ........... 260/561 S, 307 G, 307 F, 260/558 S, 559 T, 562 S, 583 EE

[56] References Cited

U.S. PATENT DOCUMENTS

| | | | |
|---|---|---|---|
| 3,318,953 | 5/1967 | Wehrmeister | 260/558 S |
| 3,414,620 | 12/1968 | Bresson et al. | 260/583 EE |
| 3,414,621 | 12/1968 | Bresson et al. | 260/583 EE |
| 3,639,395 | 2/1972 | Tomalia | 260/561 S |
| 3,682,948 | 8/1972 | Tomalia | 260/307 S |

OTHER PUBLICATIONS

Fry, J. Org. Chem. 15(1950) pp. 802–806.
Wehrmeister, J. Org. Chem. 28(1963) pp. 2587–2588.

*Primary Examiner*—Arthur P. Demers
*Attorney, Agent, or Firm*—L. Wayne White

[57] ABSTRACT

The title compounds are prepared by:

Step 1: Reacting by contacting in liquid phase (a) an aliphatic mercaptan with (b) a 2-oxazoline in the presence of (c) a small but sufficient amount of at least one transition metal salt to catalyze the reaction between (a) and (b), thereby forming an alkanamidoethyl sulfide derivative of the aliphatic mercaptan, and Step 2: Contacting the alkanamidoethyl sulfide derivative from Step 1 with an aqueous protic acid (e.g., HCl).

The transition metal salt catalysts are salts of the transition metals in groups 1b, 2b, 6b, 7b and 8, and rows 4 and 5 of the Periodic Table of the Elements, inclusive. As an example, the compound n—$C_8H_{17}$—S—$CH_2CH_2$—N-H—C(O)—$C_2H_5$ (I) was prepared in excellent yields by reacting n-octylmercaptan with 2-ethyl-2-oxazoline in the presence of a catalytic amount of hydrated cadmium chloride at a temperature of approximately 200° C and a reaction time of one hour. The compound n—$C_8H_{17}$—S—$CH_2CH_2$—$NH_2$ (II) was prepared from (I) by contacting (I) with aqueous HCl.

15 Claims, No Drawings

PROCESS FOR MAKING BETA-AMINOETHYL SULFIDES FROM ALIPHATIC MERCAPTANS AND 2-OXAZOLINES

BACKGROUND OF THE INVENTION

This invention relates to a process for making β-aminoethyl sulfide derivatives of aliphatic mercaptans. This invention also relates to a process of making derivatives of β-aminoethyl sulfides.

The literature shows that β-aminoethyl sulfides have been prepared by reacting the corresponding mercaptan with ethylenimine (i.e., aziridine). See, for example, "Ethylenimine and Other Aziridines" by O. C. Dermer and G. E. Ham, Academic Press, N.Y. (1969), pages 230–234. The references cited in the Dermer et al. text indicate that the β-aminoethyl sulfides have a variety of uses and that they are more difficult to prepare from aliphatic mercaptans than from aromatic mercaptans.

Lamb (U.S. Pat. No. 3,291,683) teaches that certain β-aminoalkyl sulfides can be prepared by reacting an alkyl mercaptan with an unsaturated nitrile (e.g., acrylonitrile) followed by chemical or catalytic reduction of the nitrile group. Lamb states that the aminoethyl sulfides are useful in controlling fungi and bacteria.

Fikentscher et al. (U.S. Pat. No. 3,793,370) teaches that β-aminoethyl sulfonium compounds are prepared by reacting a thioether with an aziridine and an acid. These compounds are, therefore, derivatives of the β-aminoethyl sulfides prepared by our process. The β-aminoethyl sulfonium compounds are curing agents, cross-linking agents, antistatic agents, emulsifiers, fungicides and valuable intermediates in the preparation of such agents.

The reaction of aromatic mercaptans with 2-oxazolines is well documented. There are only a few references which describe the reaction of aliphatic mercaptans with 2-oxazolines. None of the references utilize the class of catalysts described hereafter, so far as we are aware.

SUMMARY OF THE INVENTION

A new process has now been discovered for preparing β-aminoethyl sulfides from aliphatic mercaptans. The novel process comprises the steps of:

Step 1: Reacting by contacting in liquid phase (a) an aliphatic mercaptan with (b) a 2-oxazoline in the presence of (c) a small but sufficient amount of at least one transition metal salt to catalyze the reaction between (a) and (b), thereby forming an alkanamidoethyl sulfide derivative of the aliphatic mercaptan; and Step 2: Hydrolyzing the amide by contacting the alkanamidoethyl sulfide derivative from Step 1 with an aqueous protic acid (such as HCl).

Another aspect of our invention resides in the fact that Step 1 above is a novel process for making alkanamidoethyl sulfide derivatives of aliphatic mercaptans.

The alkanamidoethyl sulfide derivatives or the β-aminoethyl sulfide derivatives can be recovered, utilized in various areas (e.g., cross-linking of epoxy resins) or they can be derivatized to form other useful products. For example, the alkanamidoethyl sulfide derivatives can be converted to the β-aminoethyl sulfonium compounds described by Fikentscher et al. by reaction with an appropriate alkylating agent (e.g., dimethyl sulfate or benzyl chloride) followed by hydrolysis with aqueous HCl or other protic acid.

DETAILED DESCRIPTION OF THE INVENTION

The catalysts used in this invention are salts of transition metals in groups 1b, 2b, 6b, 7b and 8 and in rows 4 and 5 of the Periodic Table of the Elements, inclusive. Thus, it includes salts of chromium, manganese, iron, cobalt, nickel, copper, zinc, molybdenum, technetium, ruthenium, rhodium, palladium, silver and cadmium. The anion portion of these salts can be varied to convenience. The preferred catalysts are salts of manganese, iron, copper, zinc, silver and cadmium; and of these, the chloride, bromide, sulfate and acetates thereof are the preferred members. Cadmium chloride is the most preferred catalyst. Other suitable salts of the transition metals include, for example, those in which the anion is acetate, acetylacetonate, octoate, oxalate, benzoate, naphthanate, fluoride, bromide, chloride, nitrate, sulfate, ammonium sulfate, potassium sulfate, ammonium citrate, phosphate, molybdate, tungstate, hydroxide, and the like. Many of these salts are prepared and marketed as hydrates and such hydrates are likewise suitable for use in the instant invention.

The transition metal salt catalysts are at least partially soluble in the reaction mixture (e.g., soluble to the extent of about 0.01 weight percent or more at the reaction temperature) and the better catalysts are completely or essentially completely soluble. The known classes of transition metal salts defined above include, for example, $Cr_2Cl_3$; $Cr_2(SO_4)_3 \cdot 15H_2O$; $MnCl_2$; $MnBr_2$; $Fe[OC(CH_3):CHC(O)CH_3]_3$; $Fe(OH)_3$; $CoCl_2$; $CoSO_4 \cdot 7H_2O$; $CuF_2$; $CuCl_2$; $CuMoO_4$; $CuWO_4 \cdot 2H_2O$; $CuSO_4 \cdot 5H_2O$; $ZnCl_2$; $MoO_3$; $PdCl_2$; $AgNO_3$; $CdCl_2$; $CdBr_2$; $Cd(OOCCH_3)_2$; $Cd(OH)_2$; $CdWoO_4$; and the like.

The reactants in the instant invention are likewise known classes of compounds. The aliphatic mercaptans, for example, are aliphatic organic compounds bearing one or more mercapto (—SH) groups per molecule. Of these, the alkyl mercaptans having from 1 to about 24 carbon atoms are the preferred compounds with the alkyl mercaptans of from about 4 to about 18 carbon atoms being the most preferred, based on commercial availability.

The 2-oxazoline reactants are likewise a known class of compounds having many members; any of which can be used in this process. The preferred oxazoline reactants are those corresponding to formula III

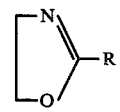

III wherein R is hydrogen or alkyl of from 1 to about 18 carbon atoms. The most preferred oxazolines are 2-H-2-oxazoline, 2-methyl-2-oxazoline and 2-ethyl-2-oxazoline. Again, the preferences are based upon commerical availability and ease of preparation. The oxazoline reactants may bear one or more ring-substituents so long as substituents are inert in the process. This then includes, for example, alkyl groups, hydroxyalkyl groups, ester groups, etc. The methods of making such compounds and their chemical reactivity has been reviewed extensively in at least 3 major review articles: (1) Wiley et al., Chemical Reviews, Vol. 44, 447 (1949); (2) Seeliger et al., Angew, Chem. International Edition, Vol. 5, No. 10, 875 (1966); and (3) Frump, Chemical Reviews, 1971, Vol. 71, 5483. A wide variety of 2-alkyl-2-oxazolines are described in the review articles. Other members of this known class can be found in patents contained in the Patent and Trademark Office under the classification of 260-307F.

Also included within the scope of suitable reactants are those compounds having an oxazoline group(s) and a mercapto group(s). For example, Tomalia et al. (U.S. Pat. No. 3,682,948) taught that desirable polymers could be formed by a thermocondensation of compound IV

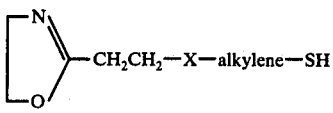   IV wherein X is oxygen or sulfur. This reaction is facilitated by use of the instant class of catalysts. Other oxazoline/mercaptan compounds are likewise known and the condensation reaction would be equal if facilitated.

Another embodiment of the invention is the reaction between various bis-oxazolines and mono- or bis-mercaptans. These types of reactions are described, for example, U.S. Pat. Nos. 3,670,046, 3,639,395 and 3,741,944.

Other embodiments of the invention will be readily apparent to those skilled in the art.

EXPERIMENTAL

The following examples will further illustrate the invention.

EXAMPLES 1–19 Preparation of
n—C$_8$H$_{17}$—S—CH$_2$CH$_2$—NH—C(O)C$_2$H$_5$

The following procedure was used for all runs. The apparatus consisted of a 100 ml, 3-necked, round-bottom flask equipped with a thermometer, water-cooled condenser, and a magnetic stirrer. n-Octylmercaptan (0.2 mole) was weighed into the reaction vessel and 2-ethyl-2-oxazoline (0.2 mole) and catalysts (0.25 mole percent) added in quick succession, and heat applied to the system. The reaction mixture was heated to reflux temperature while being vigorously stirred. A sample of the reaction mixture was taken one hour after reflux temperature was reached and immediately quenched by chilling in an ice bath, then diluted 50 percent by weight with ethanol. These samples were analyzed by gas chromatography using a commercial instrument having a metal column (1/8 inch by 10 feet) packed with 10 percent UCW 98 (a vinyl methyl silicone material sold by Union Carbide) on 60/80 mesh size Gas-Chrom Q (by The Amspec Co.). The instrument was programmed for a temperature rise of 8° C/minute between the temperatures of 130°–230° C with a hold time of 8 minutes at 230° C. A generalized area percent program was used and peak areas normalized to 100 percent to exclude the ethanol solvent peak.

The results of several experiments with different catalysts are summarized in Table I below.

TABLE I

| Ex | Catalyst | Area Percent Amide | Temperature (° C) |
|---|---|---|---|
| 1 | none | 0.65(1.08)* | 148 |

TABLE I-continued

| Ex | Catalyst | Area Percent Amide | Temperature (° C) |
|---|---|---|---|
| 2 | CrCl$_3$ . 6H$_2$O | 0.91 | 149 |
| 3 | CrO$_3$ | 3.02 | 146 |
| 4 | MnCl$_2$ | 46.38 | 169 |
| 5 | FeCl$_2$ . 4H$_2$O | 84.71 | 204 |
| 6 | FeCl$_3$ | 42.40 | 166 |
| 7 | CoCl$_2$ | 34.99 | 162 |
| 8 | NiCl$_2$ . 6H$_2$O | 0.60(2.42)* | 150 |
| 9 | CuCl | 22.53 | 157 |
| 10 | ZnO | 2.84 | 149 |
| 11 | ZnSO$_4$ . 7H$_2$O | 73.59 | 200 |
| 12 | Zn(OH)$_2$ | 22.70 | 156 |
| 13 | ZnCl$_2$ | 93.89 | 193 |
| 14 | Zn(acetate)$_2$ . 2H$_2$O | 27.70 | 159 |
| 15 | MoO$_2$ | 0.40(2.50)* | 147 |
| 16 | PdCl$_2$ | 1.14 | 149 |
| 17 | Ag$_2$SO$_4$ | 54.55 | 166 |
| 18 | Cd(acetate)$_2$ . 2H$_2$O | 87.99 | 198 |
| 19 | CdCl$_2$ . 2.5H$_2$O | 97.31 | 194 |

*Area percent amide at reaction time of 3 hours after reaching reflux temperature.

The data above show cadmium chloride to be the most effective catalyst.

In a parallel series of experiments to compare the effect of temperature, the reaction of n-octylmercaptan with 2-ethyl-2-oxazoline was conducted without catalysts, under pressure, at a temperature of 173° C. The area percent amide after 3 hours was 1.11 percent. This figure is to be compared to an identical run except conducted under atmospheric pressure and at a temperature of approximately 148° C where the area percent amide after 3 hours was 1.08 percent. From this, we concluded, that the increased reaction temperature alone was not the determining factor in the rate of reaction. The instant catalysts are indeed effective at facilitating the reaction.

EXAMPLE 20

In like manner, 2,5-dimethyl-2-oxazoline (0.2 mole) was reacted with n-tetradecylmercaptan (0.2 mole) in the presence of cadmium chloride (2.5 H$_2$O) and the product analyzed after one hour of reaction time. The area percent amide was 3.89 percent whereas a blank conducted under identical conditions was 0.13 percent.

EXAMPLE 21

In like manner, t-dodecyl mercaptan (101.0 g; 0.5 mole) was reacted with 2-ethyl-2-oxazoline (49.5 g; 0.5 mole) in the presence of 0.26 mole percent CdCl$_2$.2.5H$_2$O. The desired amide was recovered by fractional distillation in a product yield of 69.8 percent, based on reactants charged.

When this reaction was repeated using a 20 percent excess of 2-oxazoline reactant (i.e., 0.6 mole), the amide was recovered in 75.6 percent distilled yield.

EXAMPLE 22

In like manner, n-decyl mercaptan (17.4 g; 0.1 mole) was reacted with 2-H-2-oxazoline

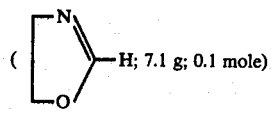

in the presence of 0.25 mole percent ZnCl$_2$ by heating the reaction mixture at a temperature of from 110°–160° C for 1.75 hours and then at 200° C for 0.5 hour. The product, H—C(O)—NH—CH$_2$CH$_2$—S—C$_{10}$H$_{21}$, was thus formed in very good yields.

Each of the above amides from Examples 1-22 was readily hydrolyzed to the corresponding aminoethyl sulfide by contacting the amide with dilute aqueous HCl.

Other compounds can be similarly prepared using other combinations of reactants and catalysts.

We claim:

1. A process for making amides comprising reacting by contacting in liquid phase (a) an aliphatic mercaptan with (b) a 2-oxazoline in the presence of (c) a small but sufficient amount of at least one transition metal salt to catalyze the reaction between (a) and (b); said transition metal salt catalyst being a salt of a metal in groups 1b, 2b, 6b, 7b, and 8 and rows 4 and 5 of the Periodic Table of the Elements, inclusive, and is at least partially soluble in the reaction mixture.

2. The process defined by claim 1 wherein (c) is a salt of manganese, iron, copper, zinc, silver or cadmium.

3. The process defined by claim 2 wherein the salt is a chloride, bromide, sulfate or acetate of said metal.

4. The process defined by claim 1 wherein (a) is an alkyl mercaptan of from 1 to about 24 carbon atoms.

5. The process defined by claim 4 wherein (a) is an alkyl mercaptan of from 4 to about 18 carbon atoms.

6. The process defined by claim 1 wherein (b) is an oxazoline of the formula

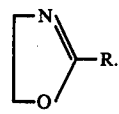

wherein R is hydrogen or an alkyl group of from 1 to about 18 carbon atoms.

7. The process defined by claim 6 wherein R is hydrogen, methyl or ethyl.

8. The process defined by claim 1 wherein (c) is cadmium chloride or a hydrate thereof.

9. The process defined by claim 8 wherein (a) is n-octylmercaptan and (b) is 2-ethyl-2-oxazoline.

10. The process defined by claim 8 wherein (a) is n-tetradecylmercaptan and (b) is 2,5-dimethyl-2-oxazoline.

11. The process defined by claim 1 comprising the additional steps of contacting the amide formed in the process of claim 1 with an aqueous protic acid to thus form the corresponding β-aminoalkyl sulfide derivative of said aliphatic mercaptan.

12. The process defined by claim 11 wherein (b) is an oxazoline of the formula

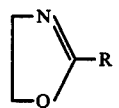

wherein R is hydrogen or an alkyl group of from 1 to about 18 carbon atoms.

13. The process defined by claim 12 wherein R is hydrogen, methyl or ethyl.

14. The process defined by claim 11 wherein said protic acid is hydrochloric acid.

15. The process defined by claim 12 wherein said acid is hydrochloric acid.

* * * * *